US009726611B2

(12) United States Patent
Nakagawa

(10) Patent No.: US 9,726,611 B2
(45) Date of Patent: Aug. 8, 2017

(54) STABILIZED ICP EMISSION SPECTROMETER AND METHOD OF USING

(71) Applicant: Hitachi High-Tech Science Corporation, Minato-ku, Tokyo (JP)

(72) Inventor: Yoshitomo Nakagawa, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 147 days.

(21) Appl. No.: 14/668,480

(22) Filed: Mar. 25, 2015

(65) Prior Publication Data

US 2015/0276611 A1 Oct. 1, 2015

(30) Foreign Application Priority Data

Mar. 26, 2014 (JP) ................. 2014-063959

(51) Int. Cl.
*G01N 21/73* (2006.01)
*G01N 21/68* (2006.01)
*G01J 3/443* (2006.01)
*H01J 49/10* (2006.01)
*H05H 1/30* (2006.01)

(52) U.S. Cl.
CPC .............. *G01N 21/73* (2013.01); *G01J 3/443* (2013.01); *G01N 21/68* (2013.01); *H01J 49/105* (2013.01); *H05H 1/30* (2013.01)

(58) Field of Classification Search
CPC .......... G01J 3/443; G01N 21/73; G01N 21/68; H05H 1/30; H01J 49/105
USPC ........................................... 356/316; 250/206
See application file for complete search history.

(56) References Cited

U.S. PATENT DOCUMENTS

| 6,541,769 | B1* | 4/2003 | Takada | H01J 49/424 250/290 |
| 2007/0296966 | A1* | 12/2007 | Benicewicz | G01J 3/2889 356/318 |
| 2010/0014741 | A1* | 1/2010 | Banville | G06K 9/6253 382/133 |
| 2010/0030719 | A1* | 2/2010 | Covey | G06F 19/24 706/48 |

(Continued)

FOREIGN PATENT DOCUMENTS

| JP | S62215850 A | 9/1987 |
| JP | H06-68467 B2 | 8/1994 |
| JP | H06-68468 B2 | 8/1994 |

*Primary Examiner* — Kara E Geisel
*Assistant Examiner* — Violeta A Prieto
(74) *Attorney, Agent, or Firm* — Banner & Witcoff, Ltd.

(57) ABSTRACT

An ICP emission spectrometer is schematically configured to include an inductively coupled plasma generation unit, a light condensing unit, a spectroscope, a detector, and a controller. The detector includes a photomultiplier and has a detector controller and an input unit. The photomultiplier has voltage dividing resistors, which make an amplification factor not to become constant immediately due to a change in an application voltage applied to the photomultiplier, but the detector controller controls an idle voltage and an idle voltage application time so that a multiplication factor becomes constant, during a period from when analysis conditions are input to the input unit in advance until a sample containing an analysis-targeted element is introduced into the inductively coupled plasma generation unit.

11 Claims, 7 Drawing Sheets

(56) References Cited

U.S. PATENT DOCUMENTS

| | | | |
|---|---|---|---|
| 2012/0112061 A1* | 5/2012 | Morokuma | H01J 49/0031 |
| | | | 250/288 |
| 2013/0173618 A1* | 7/2013 | Banville | G06F 17/30312 |
| | | | 707/736 |
| 2013/0256507 A1* | 10/2013 | Tabuchi | G01J 1/44 |
| | | | 250/206 |
| 2013/0320207 A1* | 12/2013 | Morokuma | H01J 49/0495 |
| | | | 250/288 |
| 2014/0071448 A1* | 3/2014 | Matsushita | G01N 21/68 |
| | | | 356/316 |
| 2014/0103196 A1* | 4/2014 | Soga | G01S 7/4865 |
| | | | 250/208.2 |
| 2014/0118735 A1* | 5/2014 | Matsushita | H05H 1/30 |
| | | | 356/316 |
| 2014/0154670 A1* | 6/2014 | Williams, Jr. | A61M 5/00 |
| | | | 435/5 |
| 2014/0154671 A1* | 6/2014 | Williams, Jr. | A61M 5/00 |
| | | | 435/5 |
| 2014/0301912 A1* | 10/2014 | Williams, Jr. | A61M 5/00 |
| | | | 422/547 |
| 2014/0301913 A1* | 10/2014 | Williams, Jr. | A61M 5/00 |
| | | | 422/547 |
| 2015/0190884 A1* | 7/2015 | Roy | B23K 26/127 |
| | | | 250/288 |
| 2015/0268169 A1* | 9/2015 | Ikku | G01N 21/73 |
| | | | 356/316 |
| 2015/0276484 A1* | 10/2015 | Matsuzawa | G01J 3/443 |
| | | | 356/316 |
| 2016/0267113 A1* | 9/2016 | Banville | G06F 17/30312 |

\* cited by examiner

FIG. 5

| ELEMENT | 1 | 2 | 3 | 4 | 5 | 6 | 7 | 8 | 9 | 10 |
|---|---|---|---|---|---|---|---|---|---|---|
| | As | Ca | Cd | Cr | Cu | K | Li | Na | Pb | Se |
| WAVELENGTH (nm) | 189.042 | 396.847 | 214.438 | 267.716 | 327.396 | 766.491 | 670.780 | 589.592 | 220.353 | 196.090 |
| VOLTAGE APPLIED TO DETECTOR | HIGH 800V | LOW 300V | HIGH 800V | HIGH 800V | HIGH 800V | LOW 300V | LOW 300V | LOW 300V | HIGH 800V | HIGH 800V |
| MEASUREMENT TIME (sec) | 10 | 10 | 10 | 10 | 10 | 10 | 10 | 10 | 10 | 10 |

FIG. 7

| No. | NAME OF SAMPLE | ATTRIB-UTES | As CONCEN-TRATION | Ca CONCEN-TRATION | Cd CONCEN-TRATION | Cr CONCEN-TRATION | Cu CONCEN-TRATION | K CONCEN-TRATION | Li CONCEN-TRATION | Na CONCEN-TRATION | Pb CONCEN-TRATION | Se CONCEN-TRATION |
|---|---|---|---|---|---|---|---|---|---|---|---|---|
| 1 | std1 | STANDARD SAMPLE | 0ppm | 0ppm | 0ppm | 0ppm | 0ppm | 0ppm | 0ppm | 0ppm | 0ppm | 0ppm |
| 2 | std2 | STANDARD SAMPLE | 0.5ppm | 10ppm | 0.5ppm | 0.5ppm | 0.5ppm | 10ppm | 10ppm | 10ppm | 0.5ppm | 0.5ppm |
| 3 | std3 | STANDARD SAMPLE | 1ppm | 20ppm | 1ppm | 1ppm | 1ppm | 20ppm | 20ppm | 20ppm | 1ppm | 1ppm |
| 4 | std4 | STANDARD SAMPLE | 2ppm | 50ppm | 2ppm | 2ppm | 2ppm | 50ppm | 50ppm | 50ppm | 2ppm | 2ppm |
| 5 | std5 | STANDARD SAMPLE | 5ppm | 100ppm | 5ppm | 5ppm | 5ppm | 100ppm | 100ppm | 100ppm | 5ppm | 5ppm |
| 6 | Sample1 | UNKNOWN SAMPLE | UNKNOWN | UNKNOWN | UNKNOWN | UNKNOWN | UNKNOWN | UNKNOWN | UNKNOWN | UNKNOWN | UNKNOWN | UNKNOWN |
| 7 | Sample2 | UNKNOWN SAMPLE | UNKNOWN | UNKNOWN | UNKNOWN | UNKNOWN | UNKNOWN | UNKNOWN | UNKNOWN | UNKNOWN | UNKNOWN | UNKNOWN |
| 8 | Sample3 | UNKNOWN SAMPLE | UNKNOWN | UNKNOWN | UNKNOWN | UNKNOWN | UNKNOWN | UNKNOWN | UNKNOWN | UNKNOWN | UNKNOWN | UNKNOWN |
| 9 | Sample4 | UNKNOWN SAMPLE | UNKNOWN | UNKNOWN | UNKNOWN | UNKNOWN | UNKNOWN | UNKNOWN | UNKNOWN | UNKNOWN | UNKNOWN | UNKNOWN |
| 10 | Sample5 | UNKNOWN SAMPLE | UNKNOWN | UNKNOWN | UNKNOWN | UNKNOWN | UNKNOWN | UNKNOWN | UNKNOWN | UNKNOWN | UNKNOWN | UNKNOWN |
| 11 | Sample6 | UNKNOWN SAMPLE | UNKNOWN | UNKNOWN | UNKNOWN | UNKNOWN | UNKNOWN | UNKNOWN | UNKNOWN | UNKNOWN | UNKNOWN | UNKNOWN |
| 12 | Sample7 | UNKNOWN SAMPLE | UNKNOWN | UNKNOWN | UNKNOWN | UNKNOWN | UNKNOWN | UNKNOWN | UNKNOWN | UNKNOWN | UNKNOWN | UNKNOWN |
| 13 | Sample8 | UNKNOWN SAMPLE | UNKNOWN | UNKNOWN | UNKNOWN | UNKNOWN | UNKNOWN | UNKNOWN | UNKNOWN | UNKNOWN | UNKNOWN | UNKNOWN |
| 14 | Sample9 | UNKNOWN SAMPLE | UNKNOWN | UNKNOWN | UNKNOWN | UNKNOWN | UNKNOWN | UNKNOWN | UNKNOWN | UNKNOWN | UNKNOWN | UNKNOWN |
| 15 | Sample10 | UNKNOWN SAMPLE | UNKNOWN | UNKNOWN | UNKNOWN | UNKNOWN | UNKNOWN | UNKNOWN | UNKNOWN | UNKNOWN | UNKNOWN | UNKNOWN |

STABILIZED ICP EMISSION SPECTROMETER AND METHOD OF USING

This application claims priority from Japanese Patent Application No. 2014-063959 filed on Mar. 26, 2014, the entire subject-matter of which is incorporated herein by reference.

BACKGROUND

1. Technical Field

The present disclosure relates to an Inductively Coupled Plasma (ICP) emission spectrometer for analyzing elements (for example, trace impurity elements) contained in a solution sample.

2. Description of the Related Art

An ICP emission spectrometer atomizes or ionizes a solution sample for ICP emission spectroscopy by using inductively coupled plasma (ICP), and performs a spectroscopy analysis on atomic emission lines (spectral lines) emitted at that time so as to perform a quantitative analysis and a qualitative analysis on trace impurity elements. Then, the ICP emission spectrometer identifies elemental species from a wavelength of a detected atomic emission line, and calculates concentration of trace elements based on intensity thereof. However, the intensity of the atomic emission line varies depending on the elemental species or element-containing concentration, and even the same element has the atomic emission line of various wavelengths. Accordingly, the intensity varies depending on which atomic emission line is selected. Furthermore, characteristics of the ICP emission spectrometer show that detection efficiency varies depending on the wavelength of the atomic emission line. An ICP emission spectrometer is known which can accurately analyze a wider concentration range for much more elements (for example, refer to JP-B-H06-68467 and JP-B-H06-68468).

JP-B-H06-68467 discloses a photometric device for emission spectroscopic analysis which includes means for changing an amplification degree of a photomultiplier by comparing a detection output of the photomultiplier with a reference value and by feeding back a comparison output to an application voltage of the photomultiplier, and means for calculating a photometric value as a ratio between the detection output and the amplification degree by detecting the application voltage, and by converting the application voltage into the amplification degree using correlation data between the application voltage and the amplification degree which are stored in advance. According to this photometric device for emission spectroscopic analysis, unlike the device in the related art, it is not necessary to set sensitivity for each element in advance after estimating an amount of each element contained in a sample. JP-B-H06-68467 discloses that sensitivity adjustment can be fully automated and an excellent SN ratio can be maintained in a wider dynamic range.

JP-B-H06-68468 discloses an ICP emission spectrometer in which multiple samples whose concentration of analysis elements is changed at a substantially constant ratio are prepared, the respective samples are introduced into a plasma torch so as to emit light, which measures spectral intensity of the respective samples caused to emit the light in each negative high pressure by changing the negative high pressure applied to a photomultiplier, and which determines the correlation of a gain for each negative high pressure based on a measurement value of the spectral intensity of the respective samples. According to this ICP emission spectrometer, it is possible to accurately determine a gain calibration curve of the photomultiplier by adjusting concentration of an analysis sample. Thus, a light source lamp can be omitted. Therefore, JP-B-H06-68468 discloses that the ICP emission spectrometer can further reduce costs as compared to that in the related art.

SUMMARY

According to JP-B-H06-68467 and JP-B-H06-68468, it is possible to measure wider range of light intensity by changing a voltage applied to the photomultiplier (detector). However, if a high voltage applied to the photomultiplier is changed, a multiplication factor is not immediately brought into a steady state, and approximately three minutes to five minutes are required, thereby causing a problem in that accuracy of quantitative results becomes poor temporarily.

Therefore, the present disclosure provides an ICP emission spectrometer which enables a main analysis to be quickly performed by applying a voltage to a photomultiplier in advance.

In one aspect of the disclosure, an ICP emission spectrometer comprises: an inductively coupled plasma generation unit configured to atomize or ionize an analysis-targeted element using inductively coupled plasma to obtain atomic emission lines; a light condensing unit configured to converge the atomic emission lines; a spectroscope configured to detect the atomic emission lines by diffracting light after receiving the atomic emission lines through a light incident window; a detector configured to detect the light passing through the spectroscope; a detector controller configured to control a voltage applied to the detector and an application time of the voltage; and an input unit for receiving an operation input of analysis conditions corresponding to the analysis-targeted element, wherein the detector controller is configured to control the voltage applied to the detector and the application time thereof based on an idle voltage and an idle voltage application time corresponding to an expected power amount obtained from an analysis voltage applied to the detector and an analysis voltage application time under the analysis conditions during a period from when the analysis conditions are input to the input unit until a sample containing the analysis-targeted element is introduced into the inductively coupled plasma generation unit.

The detector controller may be configured to set the idle voltage and the idle voltage application time to have a voltage application cycle which is similar to a voltage application cycle determined by the analysis voltage and the analysis voltage application time.

The detector controller may be configured to set the idle voltage to have a high voltage and a low voltage identical to a high voltage and a low voltage in the analysis voltage and to set the idle voltage application time to have an application time ratio of a high voltage application time to a low voltage application time which are identical to an application time ratio of a high voltage application time and a low voltage application time in the analysis voltage.

The detector controller may be configured to set a constant voltage as the idle voltage, the constant voltage having a power amount identical to an average power amount determined by the analysis voltage and the analysis voltage application time.

The detector controller may be configured to set the idle voltage and the idle voltage application time per one cycle to have a voltage application pattern that is the same as a voltage application pattern determined by the analysis voltage and the analysis voltage application time per one cycle.

According to the present disclosure, a quantitative analysis is performed by waiting until an amplification factor of a photomultiplier of a detector becomes constant. Therefore, it is possible to provide an ICP emission spectrometer which can ensure accuracy of the quantitative analysis.

BRIEF DESCRIPTION OF THE DRAWINGS

FIGS. 3A and 3B illustrate a photomultiplier of a detector in the ICP emission spectrometer according to the present disclosure, in which FIG. 3A is a schematic front view, and FIG. 3B is a schematic view of an electron multiplier;

FIG. 5 is a table illustrating selected condition examples of the quantitative analysis in the ICP emission spectrometer according to the present disclosure;

FIGS. 6A to 6C are chart graphs illustrating a cycle of an idle voltage on the assumption of an analysis voltage in setting the quantitative analysis conditions based on the table in FIG. 5, in which FIG. 6A illustrates an example of the idle voltage with the cycle which is the same as the cycle of the analysis voltage in the quantitative analysis conditions, FIG. 6B illustrates an example of the idle voltage with an application time ratio which is identical to each application time ratio of a high voltage and a low voltage in the analysis voltage, and FIG. 6C illustrates an example of the idle voltage with an average voltage in the analysis voltage; and FIG. 7 is a table illustrating sample condition examples in the ICP emission spectrometer according to the present disclosure.

DETAILED DESCRIPTION

Hereinafter, a preferred embodiment of an ICP emission spectrometer according to the present disclosure will be described in detail with reference to FIGS. 1 to 7.

Figure 1:
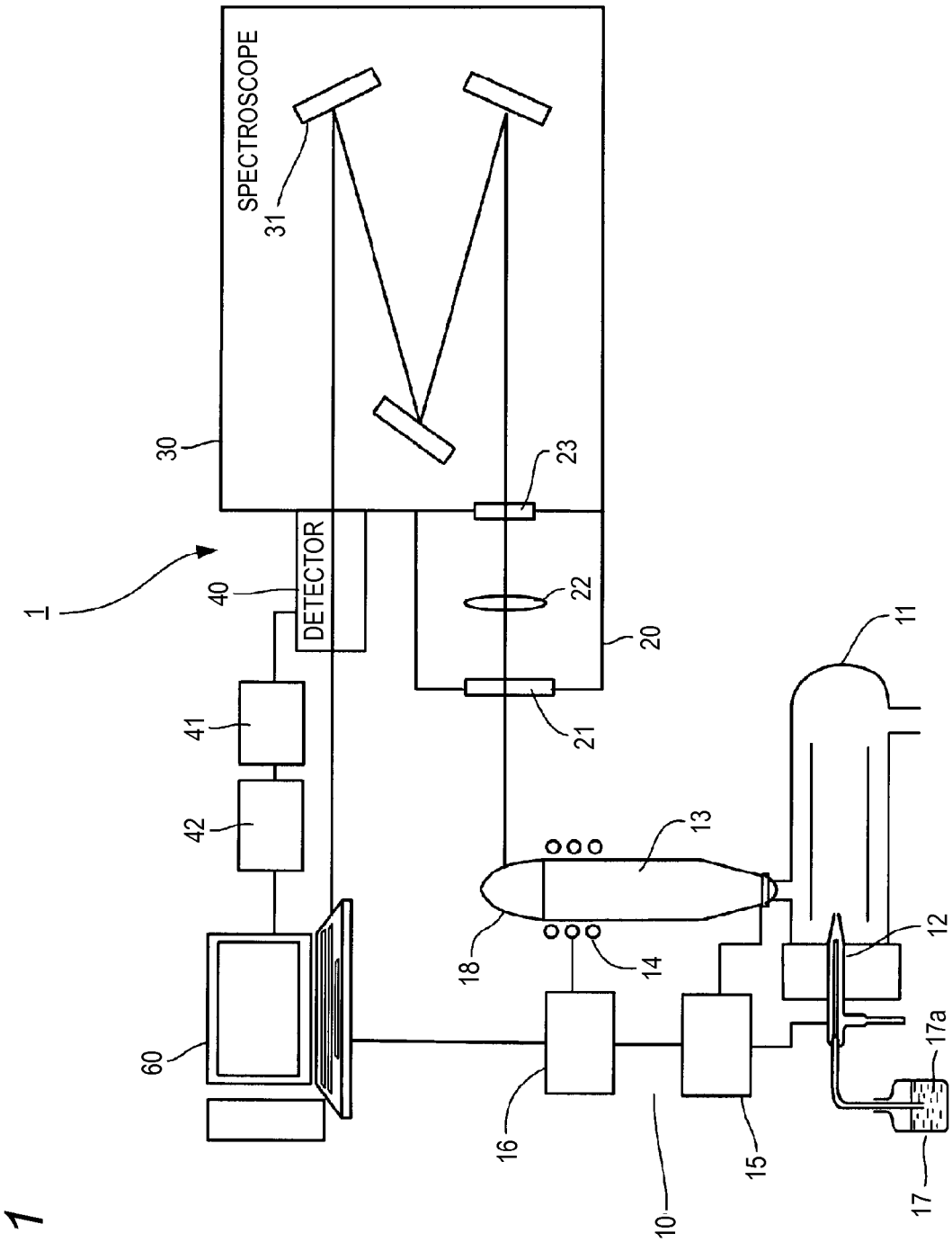
FIG. 1 is a conceptual diagram illustrating an example of an ICP emission spectrometer according to the present disclosure.

FIG. 1 is a conceptual diagram illustrating an example of the ICP emission spectrometer according to the present disclosure.

An ICP emission spectrometer 1 is schematically configured to include an inductively coupled plasma generation unit 10, a light condensing unit 20, a spectroscope 30, a detector 40, and a controller 60. The inductively coupled plasma generation unit 10 is schematically configured to include a spray chamber 11, a nebulizer 12, a plasma torch 13, a high frequency coil 14, a gas controller 15, and a high frequency power source 16. The light condensing unit 20 for condensing atomic emission lines is arranged between the inductively coupled plasma generation unit 10 and the spectroscope 30, and includes a light incident slit 21, a light condensing lens 22, and a light incident window 23.

The spectroscope 30 for diffracting and detecting the atomic emission lines includes an optical component 31 such as a diffraction grating and a mirror. The detector 40 for detecting light passing through the spectroscope 30 has a photomultiplier 70 (to be described later). In addition, the detector 40 includes a detector controller 41 for controlling a voltage applied to the detector 40 and a voltage application time, and an input unit 42 for receiving an operation input of analysis conditions corresponding to an analysis-targeted element. The detector controller 41 and the input unit 42 may be included in a controller 60 configured to have a computer or the like.

Carrier gas (argon gas) supplied into the nebulizer 12 is ejected from a distal end of the nebulizer 12 into the spray chamber 11, negative pressure suction of the carrier gas sucks up a solution sample 17a of a sample container 17, thereby ejecting the solution sample 17a from the distal end of the nebulizer 12. The ejected solution sample 17a is allowed to have uniformized particles and stabilized air flows inside the spray chamber 11, and is controlled by the gas controller 15 so as to be introduced into the plasma torch 13. Then, a high frequency current is caused to flow into the high frequency coil 14 from the high frequency power source 16. Sample molecules (or atoms) of the solution sample 17a are heated and excited so as to emit light, thereby generating an inductively coupled plasma 18 (hereinafter, referred to as a plasma) above the plasma torch 13. Frequency of the high frequency current is generally 27.12 MHz or 40 MHz.

The solution sample 17a is a standard sample whose concentration of contained elements is known and which is used in creating a calibration curve, or an unknown sample whose concentration a user wants to know. Replacement of the solution sample 17a into the sample container 17 can be performed manually or automatically by using an automatic sampler or the like.

Figure 2:
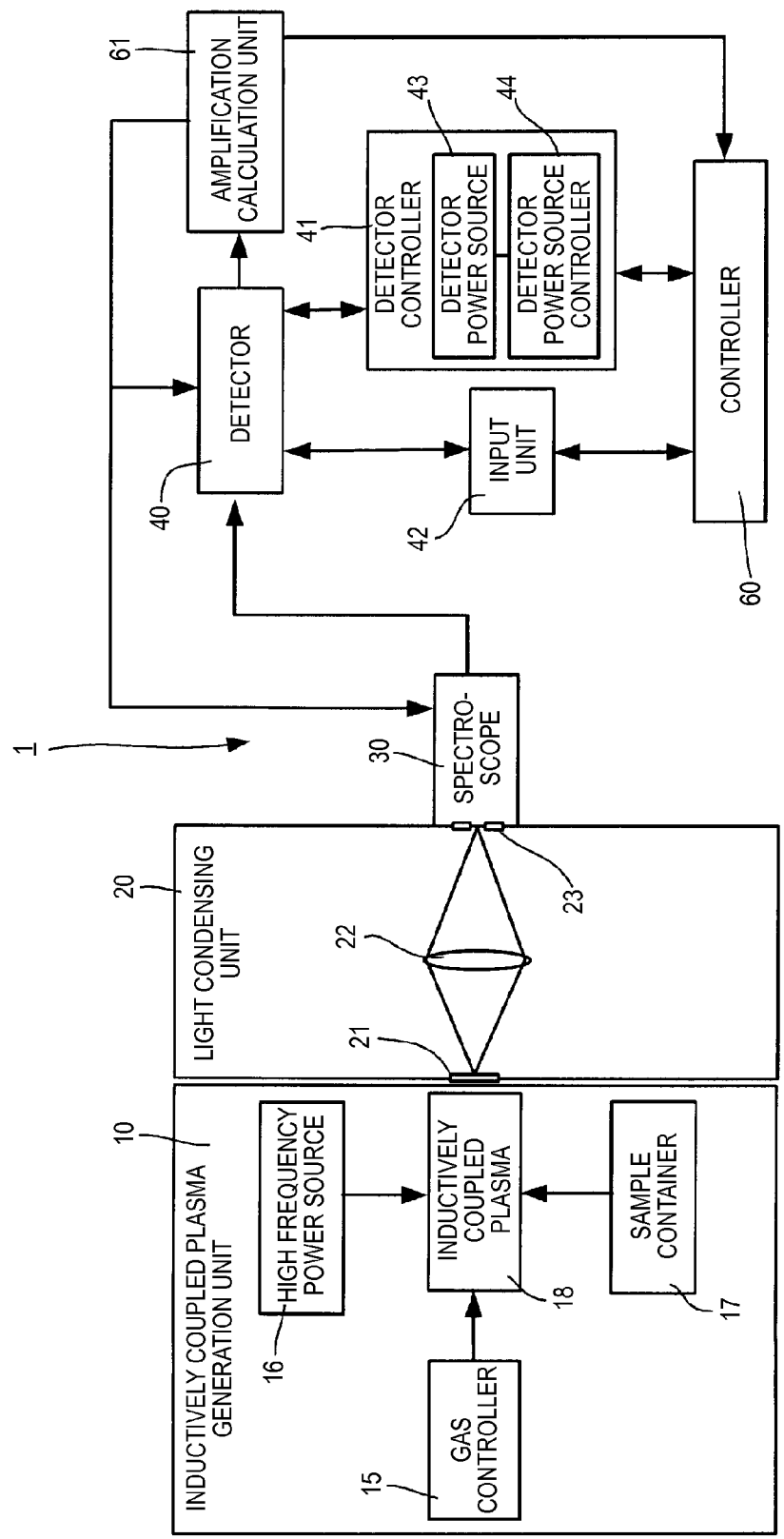
FIG. 2 is a block diagram illustrating an example of the ICP emission spectrometer according to the present disclosure.

FIG. 2 is a block diagram illustrating an example of the ICP emission spectrometer according to the present disclosure.

The atomic emission lines in which an analysis-targeted element of the solution sample 17a is atomized or ionized by the plasma 18 are incident on the light condensing unit 20 for condensing the atomic emission lines, and pass through the light incident slit 21 and the light condensing lens 22. After passing through the light incident window 23, the atomic emission lines are incident in the inside of the spectroscope 30. As the spectroscope 30, a Czerny-Turner spectroscope, an Echelle spectroscope, a Paschen-Runge spectroscope, or the like is used.

The atomic emission lines received through the light incident window 23 are diffracted and detected by the optical component 31 inside the spectroscope 30, are incident on the detector 40, and are detected by the detector 40. The detected atomic emission lines are analyzed by data processing in the controller 60 or the like. A qualitative analysis is performed on the analysis-targeted element (for example, trace impurity element) contained in the solution sample 17a, based on a wavelength of the atomic emission lines (spectral lines), and a quantitative analysis is performed on the analysis-targeted element, based on intensity of the atomic emission lines (spectral lines).

The detector controller 41 of the detector 40 has a detector power source 43 and a detector power source controller 44. The detector power source 43 supplies an application voltage up to approximately negative 1000 V to the detector 40, and supplies a current up to approximately 0.3 mA corresponding to an application voltage Ve to the detector 40. The detector power source controller 44 controls turning on/off of a voltage value of the voltage generated by the detector 40.

A signal of the atomic emission lines which passes through the spectroscope 30 and is detected by the detector 40 is amplified by an amplification calculation unit 61, and is recorded as measurement data by the controller 60. The amplification calculation unit 61 performs wavelength-swept control for the spectroscope 30, and performs control of an integration time or the like for the detector 40.

Figure 3A:
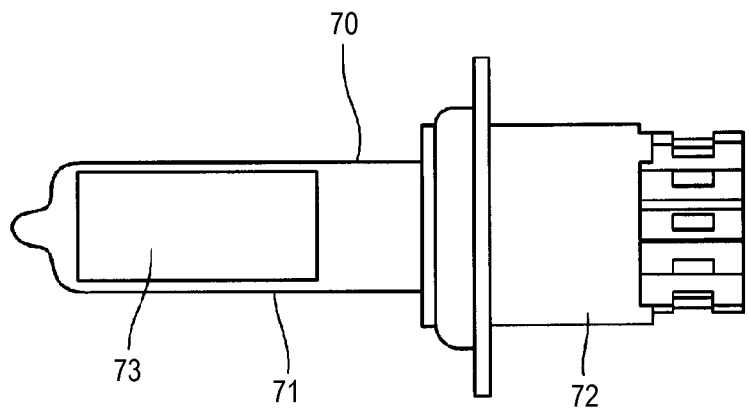
Figure 3B:
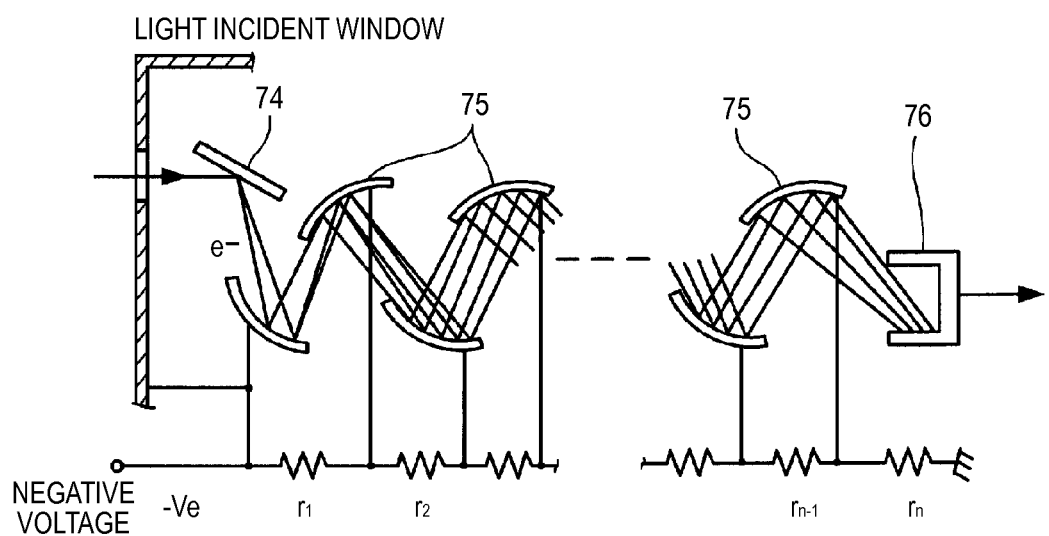

FIGS. 3A and 3B illustrate the photomultiplier of the detector. FIG. 3A is a schematic front view, and FIG. 3B is a schematic view of an electron multiplier.

The photomultiplier 70 is used for the detector 40. The photomultiplier 70 is configured to include a spherical body portion 71 formed of quartz glass and a socket portion 72. The spherical body portion 71 includes an electron multiplier 73, and the socket portion 72 includes multiple voltage dividing resistors $r_1$ to $r_n$.

The photomultiplier 70 converts incident light of the atomic emission lines into a photoelectron ($e^-$) by using a photoelectric surface 74 of the electron multiplier 73. The converted photoelectron collides with a dynode 75 so as to emit a secondary electron, and is continuously multiplied while colliding with multiple dynodes 75. That is, in the photomultiplier 70, the application voltage Ve for optoelectronic acceleration is applied to the dynode 75 via the respective voltage dividing resistors $r_1$ to $r_n$, and the excited and emitted photoelectron is sequentially multiplied by the photoelectron colliding with the dynode 75. A current value corresponding to light intensity is output to the multiplied photoelectron from a collector 76.

Figure 4:
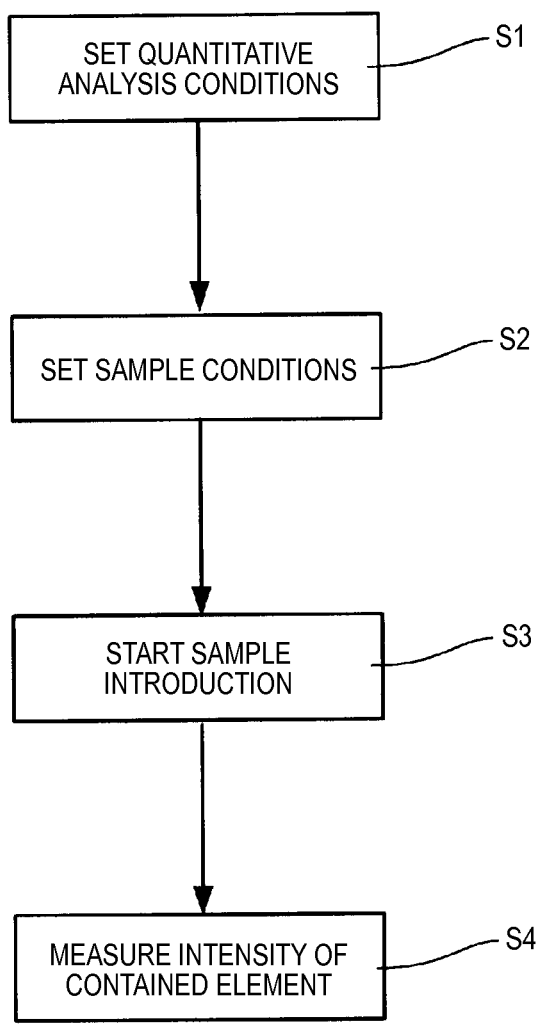
FIG. 4 is a flowchart illustrating a flow of a quantitative analysis in the ICP emission spectrometer according to the present disclosure.

FIG. 4 is a flowchart illustrating a flow of the quantitative analysis.

When conditions of the quantitative analysis are set (Step S1), plasma operation conditions (high frequency power, gas conditions, or the like), detection conditions (elements and wavelengths which are to be detected, and measurement time for each element), correction conditions (internal standard correction or baseline correction), or the like are set.

When sample conditions are set (Step S2), attributes of a sample to be measured (whether the sample is a standard sample or an unknown sample), elemental species contained in the standard sample and concentration thereof, a name of the unknown sample, sampling conditions in a case of an automatic analysis using an automatic sampler (attributes and names of the samples arrayed side by side on a sample stage, a measurement sequence, and a replacement time when the sample is replaced), or the like are set.

When sample introduction is started (Step S3), intensity measurement of the contained element is started after replacing with a sample to be measured and confirming whether the introduction of the sample is stabilized (Step S4). When the automatic sampler is used, the measurement of the contained element is started after waiting for a predetermined time instead of confirming whether the introduction of the sample is stabilized.

When an accurate quantitative analysis is performed, it is necessary to stabilize a multiplication factor of the photomultiplier 70 used for the detector 40. However, even when the application voltage Ve is changed, the multiplication factor is not immediately brought into a steady state (constant sate). That is, a voltage in which the application voltage Ve is divided by the voltage dividing resistors $r_1$ to $r_n$ is applied to the dynode 75 of the photomultiplier 70. However, if the application voltage Ve is changed, a current flowing in the voltage dividing resistors $r_1$ to $r_n$ is changed to reach several hundred microamperes. For this reason, a calorific value of the voltage dividing resistors $r_1$ to $r_n$ is changed, and a temperature of the voltage dividing resistors $r_1$ to $r_n$ and the dynode 75 is changed. Consequently, the amplification factor does not become constant immediately.

In other words, the stabilization of the amplification factor depends on whether heat generated from the voltage dividing resistors $r_1$ to $r_n$ of the photomultiplier 70 is stabilized. That is, an equation of calorific value Q=power P×time t (one in a case of a unit time)=current I×voltage V×t=$V^2$/R (resistance of the voltage dividing resistors) is satisfied. Accordingly, the amplification factor may be stabilized if heat generated by the application voltage Ve applied during a predetermined time is constant on average.

FIG. 5 is a table illustrating selected condition examples of the quantitative analysis.

In the present disclosure, the ICP emission spectrometer 1 is operated (warming-up operation) in advance in a form modeled on conditions of the quantitative analysis in a main analysis as illustrated in FIG. 5. The calorific value of the voltage dividing resistors $r_1$ to $r_n$ of the photomultiplier 70 is caused to correspond to the calorific value during the main analysis. In this manner, the main analysis is allowed to be quickly performed.

For example, an analysis voltage which is the application voltage Ve of the detector 40 (photomultiplier 70) is applied in a range where a high voltage is 800 V and low voltage is 300 V. According to the conditions of the quantitative analysis based on the table, six elements per 60 seconds are measured by the "high" analysis voltage, and four elements per 40 seconds are measured by the "low" analysis voltage. The ratio of the analysis application time of the analysis voltage of the detector 40 is 60% in a case of the high voltage, and is 40% in a case of the low voltage. One cycle time in the main analysis represents 100 seconds (=10 seconds×10). Then, one cycle of an idle voltage of the detector 40 which is applied after setting the conditions of the quantitative analysis is shortened to 10 seconds (one tenth of one cycle in the main analysis), thereby setting a ratio of an idle voltage application time when the "high" analysis voltage is applied for six seconds and the "low" analysis voltage is applied for four seconds within 10 seconds. The cycle is repeated until the sample introduction is started.

During a period from when the sample introduction is started until the contained element measurement is started, the idle voltage (high voltage when As is measured) of the detector 40 is set for the element to be measured. In the related art in which conditions of the voltage applied to the detector 40 before the contained element is measured are not constant, a CV value (=standard deviation/average value) of the quantitative measurement result is approximately 1% in some cases. In the present disclosure, conditions of the idle voltage applied to the detector 40 are controlled during the idle voltage application time from when the sample introduction is started until the contained element measurement is started. Accordingly, the CV value of the quantitative measurement result is improved to reach approximately 0.2%.

Here, the "analysis voltage" represents a voltage applied to the detector 40 for the contained element which is a quantitative analysis target based on the quantitative analysis conditions or the sample analysis conditions which are input to the input unit 42. The "analysis voltage application time" represents a time when the analysis voltage is applied during the quantitative analysis. In addition, the "idle voltage" represents a voltage corresponding to an estimated power amount obtained from an actual analysis voltage and an actual analysis voltage application time. The "idle voltage application time" represents a time when the idle voltage is applied until the idle voltage reaches the analysis voltage. The "idle voltage" and the "idle voltage application time" are used in a so-called warming-up operation or idling operation in order to cause the photomultiplier 70 of the detector 40 to have the same (substantially identical) heat generation in advance before an actual quantitative analysis is performed. The quantitative analysis is performed by waiting until the amplification factor of the photomultiplier 70 becomes constant (steady). In this manner, the accurate quantitative analysis can be ensured.

Then, the detector controller 41 controls the detector 40, during a period from when the analysis conditions are input to the input unit 42 until the solution sample 17a containing the analysis-targeted element is introduced into the inductively coupled plasma generation unit 10, based on the idle voltage and the idle voltage application time of the idle voltage corresponding to the expected power amount obtained from the analysis voltage applied to the detector 40 under the analysis conditions and the analysis voltage application time of the analysis voltage.

Figure 6A:
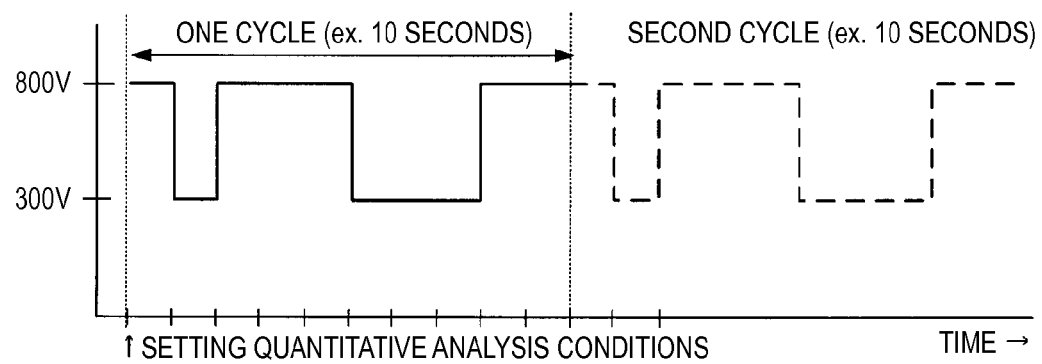
Figure 6B:
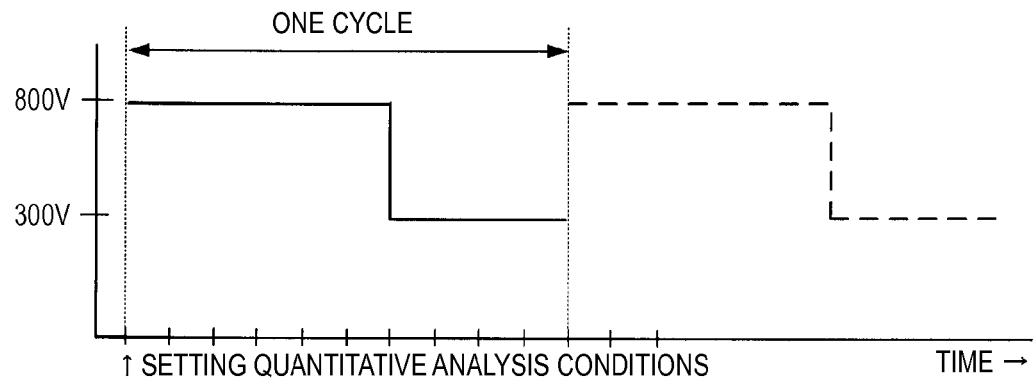
Figure 6C:
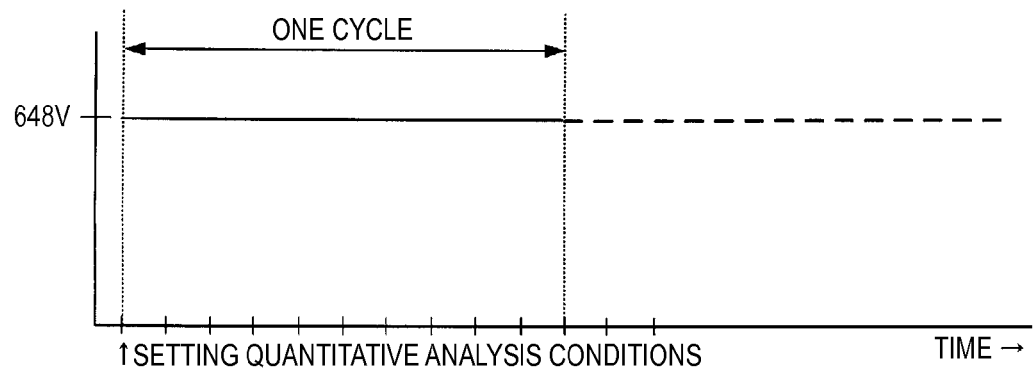

FIGS. 6A to 6C are chart graphs illustrating a cycle of the idle voltage on the assumption of the analysis voltage in setting the quantitative analysis conditions based on the table in FIG. 5. FIG. 6A illustrates an example of the idle voltage with the cycle which is the same as the cycle of the analysis voltage in the quantitative analysis conditions. FIG. 6B illustrates an example of the idle voltage with an application time ratio which is identical to each application time ratio of a high voltage and a low voltage in the analysis voltage. FIG. 6C illustrates an example of the idle voltage with an average voltage in the analysis voltage. The vertical axis represents the application voltage, and the horizontal axis represents the time.

FIG. 6A illustrates a method of repeating the cycle for applying a voltage which is identical to the analysis voltage in the quantitative analysis conditions. However, as described above, 100 seconds (refer to FIG. 5) of one cycle time in the quantitative analysis conditions are shortened to 10 seconds. A change between 800 V and 300 V is set based on the table in FIG. 5. Then, the detector controller 41 sets the idle voltage and the idle voltage application time so as to have a voltage application cycle which is the same as a voltage application cycle determined by the analysis voltage and the analysis voltage application time. The term of "same" used herein does not mean exactly the same time, but means that one cycle in the main analysis (100 seconds) is similar to one cycle in the idling (10 seconds) in terms of the voltage applied to the detector 40 and a time ratio of the application time of the voltage in one voltage application cycle, in other words, means that a voltage application pattern per one cycle in the idling is the same as a voltage application pattern per one cycle in the main analysis.

In FIG. 6B, the voltage application cycle is repeated so that a ratio between the high application voltage and the low application voltage is set in accordance with the quantitative analysis conditions. That is, 60% represents 800 V, and 40% represents 300 V. Then, the detector controller 41 sets the idle voltage and the idle voltage application time with the high voltage and the low voltage and each application time ratio thereof which are the same as the high voltage and the low voltage in the analysis voltage and each application time ratio.

In FIG. 6C, a constant idle voltage for performing a warming-up operation is set so as to be equal to an average heat generation amount based on the quantitative analysis conditions. That is, an idle voltage value becomes 648 [V], based on an equation of $(V^2/R)=(800^2/R\times0.6+300^2/R\times0.4)$. Then, the detector controller 41 sets a voltage which is identical to an average voltage determined by the analysis voltage and the analysis voltage application time, as the idle voltage.

If the quantitative analysis conditions are set (Step S1), the detector power source controller 44 of the detector controller 41 sends a control signal to the detector power source 43 so that the idle voltage is applied to the detector 40 in the cycle matching the ratio of the idle voltage value and the idle voltage application time for detecting the contained element. For example, the quantitative analysis is performed on one sample, an element 1 is measured for a time period α using an analysis voltage value A, and then an element 2 is measured for a time period β using an analysis voltage value B. In this case, in the control signal, an idle voltage value A is applied at the ratio of the idle voltage application time of α/(α+β) within one cycle, and an idle voltage value B is applied at the ratio of the idle voltage application time of β/(α+β). Then, the detector 40 is caused to continuously repeat the voltage application cycle in accordance with the control signal.

FIG. 7 is a table illustrating an example of sample conditions.

When the sample conditions are set (Step S2), the name of samples, attributes, and the concentration of the element contained in the standard sample are input to the input unit 42. When the automatic sampler is used, a position of each sample placed on a sample stage or a replacement time when the sample introduction is replaced is also input thereto. The time required until the detector 40 becomes constant when the analysis voltage is changed is approximately five minutes. Accordingly, the time for stabilizing the detector 40 is set to five minutes. The sample conditions are input manually, and it takes five minutes to carry out setting work. In this case, the analysis voltage application time from when the quantitative analysis is set until the contained element is measured is equal to or longer than the time for stabilizing the detector 40. Therefore, the contained element can be measured without any changes.

When a file having previously created sample condition setting is read out, the setting work is completed in a short time. In this case, the analysis voltage application time from when the quantitative analysis is set until the contained element is measured is shorter than the time for stabilizing the detector 40. Therefore, the actual measurement is performed after the lapse of the time for stabilizing the detector 40. In the related art, the CV value of the quantitative measurement result is approximately 1%. However, according to the present disclosure, the CV value of the quantitative measurement result is improved to reach approximately 0.2%.

The setting time for the sample condition setting (Step S2) is not constant. When there are a large number of standard samples to be measured or a large number of unknown samples, and when there are large number of elements to be measured per one sample, it takes a long time to perform the input work, thereby lengthening the setting time for the sample conditions. In addition, when the analysis is performed in accordance with the previously created sample conditions, the setting time is shortened since only the setting conditions are invoked. If the setting for the sample conditions is completed in a short time and the measurement is immediately started, the measurement is performed in a state where the amplification factor of the photomultiplier 70 has not become constant, thereby causing accuracy of the quantitative analysis to be poor.

In the present disclosure, when the idle voltage application time of the photomultiplier 70 is set and the sample conditions are set in a short time, the measurement for the contained element is started after waiting so that the idle voltage application time from when the quantitative analysis conditions are set until the measurement for the contained element is started is equal to or longer than the time for stabilizing the photomultiplier 70. That is, the time from when the quantitative analysis conditions are set (Step S1) until the intensity measurement for the contained element is performed (Step S4) may be equal to or longer than the time for stabilizing the detector 40.

Without being limited to the above-described embodiment, the present disclosure can be appropriately modified or improved. In addition, materials, shapes, dimensions, values, forms, the number, arrangement locations, or the like of the respective configuration elements in the above-described embodiment are optionally selected as long as the present disclosure can be achieved, and do not limit the present disclosure.

An ICP emission spectrometer according to the present disclosure can be applied to use which can ensure accuracy of a quantitative analysis by performing the quantitative analysis after waiting until an amplification factor of a photomultiplier of a detector becomes constant.

What is claimed is:

1. An ICP emission spectrometer comprising:
    an inductively-coupled plasma generator configured to atomize or ionize an analysis-targeted element using inductively coupled plasma to obtain atomic emission lines;
    a light condenser configured to converge the atomic emission lines;
    a spectroscope configured to detect the atomic emission lines by diffracting light after receiving the atomic emission lines through a light incident window;
    a detector configured to detect the light passing through the spectroscope;
    a detector controller configured to control a voltage applied to the detector and an application time of the voltage; and
    an input device for receiving an operation input of analysis conditions corresponding to the analysis-targeted element,
    wherein the detector controller is configured to:
        stabilize the detector by controlling, prior to a sample containing the analysis-targeted element into the inductively-coupled plasma generator the voltage applied to the detector and the application time thereof based on an idle voltage and an idle voltage application time corresponding to an expected power amount obtained from an analysis voltage applied to the detector and an analysis voltage application time under the analysis conditions during a period from when the analysis conditions are input to the input device until a sample containing the analysis-targeted element will be introduced into the inductively-coupled plasma generator.

2. The ICP emission spectrometer according to claim 1, wherein the detector controller is configured to set the idle voltage and the idle voltage application time to have a voltage application cycle which is similar to a voltage application cycle determined by the analysis voltage and the analysis voltage application time in terms of the voltage applied to the detector and a time ratio of the application time of the voltage in one voltage application cycle.

3. The ICP emission spectrometer according to claim 1, wherein the detector controller is configured to set the idle voltage to have a high voltage and a low voltage identical to a high voltage and a low voltage in the analysis voltage and to set the idle voltage application time to have an application time ratio of a high voltage application time to a low voltage application time which are identical to an application time ratio of a high voltage application time and a low voltage application time in the analysis voltage.

4. The ICP emission spectrometer according to claim 1, wherein the detector controller is configured to set a constant voltage as the idle voltage, the constant voltage having a power amount identical to an average power amount determined by the analysis voltage and the analysis voltage application time.

5. The ICP emission spectrometer according to claim 1, wherein the detector controller is configured to set the idle voltage and the idle voltage application time per one cycle to have a voltage application pattern that is the same as a voltage application pattern determined by the analysis voltage and the analysis voltage application time per one cycle.

6. A method comprising:
    atomizing or ionizing, by an inductively-coupled plasma generator, an analysis-targeted element using inductively coupled plasma to obtain atomic emission lines;
    converging the atomic emission lines;
    detecting the atomic emission lines by diffracting light after receiving the atomic emission lines through a light incident window;
    detecting, by a detector, the light passing through a spectroscope;
    receiving an operation input of analysis conditions corresponding to the analysis-targeted element;
    stabilizing the detector by controlling a voltage applied to the detector and an application time thereof based on an idle voltage and an idle voltage application time corresponding to an expected power amount obtained from an analysis voltage applied to the detector and an analysis voltage application time under the analysis conditions during a period from when the analysis conditions are input until a sample containing the analysis-targeted element will be introduced into the inductively-coupled plasma generator; and
    introducing the sample containing the analysis-targeted element into the inductively-coupled plasma generator when the detector becomes stabilized.

7. The method according to claim 6, further comprising:
    setting the idle voltage and the idle voltage application time to have a voltage application cycle which is similar to a voltage application cycle determined by the analysis voltage and the analysis voltage application time in terms of the voltage applied to the detector and a time ratio of the application time of the voltage in one voltage application cycle.

8. The method according to claim 6, further comprising:
    setting the idle voltage to have a high voltage and a low voltage identical to a high voltage and a low voltage in the analysis voltage and to set the idle voltage application time to have an application time ratio of a high voltage application time to a low voltage application time which are identical to an application time ratio of a high voltage application time and a low voltage application time in the analysis voltage.

9. The method according to claim 6, further comprising:
    setting a constant voltage as the idle voltage, the constant voltage having a power amount identical to an average power amount determined by the analysis voltage and the analysis voltage application time.

10. The method according to claim 6, further comprising:
    setting the idle voltage and the idle voltage application time per one cycle to have a voltage application pattern that is the same as a voltage application pattern determined by the analysis voltage and the analysis voltage application time per one cycle.

11. A method comprising:

atomizing or ionizing, by an inductively-coupled plasma generator, an analysis-targeted element using inductively coupled plasma to obtain atomic emission lines;

converging the atomic emission lines;

detecting the atomic emission lines by diffracting light after receiving the atomic emission lines through a light incident window;

detecting, by a detector, the light passing through a spectroscope;

receiving an operation input of analysis conditions corresponding to the analysis-targeted element;

applying a voltage to the detector during a period from when the analysis conditions are input prior to a sample containing the analysis-targeted element being introduced into the inductively-coupled plasma generator, the applying the voltage including applying an idle voltage to the detector until the idle voltage reaches an analysis voltage corresponding to an expected power amount obtained from an analysis voltage applied to the detector and an analysis voltage application time; and introducing the sample containing the analysis-targeted element into the inductively-coupled plasma generator based on when the idle voltage reaches the analysis voltage.

* * * * *